United States Patent
DeLeo et al.

(10) Patent No.: US 7,943,588 B2
(45) Date of Patent: May 17, 2011

(54) METHOD FOR PREVENTING OR TREATING NEUROPATHIC PAIN

(75) Inventors: Joyce A. DeLeo, Lebanon, NJ (US); Flobert Y. Tanga, Medford, MA (US)

(73) Assignee: Trustees of Dartmouth College, Hanover, NH (US)

( * ) Notice: Subject to any disclaimer, the term of this patent is extended or adjusted under 35 U.S.C. 154(b) by 1084 days.

(21) Appl. No.: 11/691,783

(22) Filed: Mar. 27, 2007

(65) Prior Publication Data

US 2007/0244066 A1    Oct. 18, 2007

Related U.S. Application Data

(60) Provisional application No. 60/786,643, filed on Mar. 28, 2006.

(51) Int. Cl.
*A61K 48/00* (2006.01)
*A61K 39/395* (2006.01)
*A61K 45/00* (2006.01)
*C07H 21/04* (2006.01)
*C07K 16/00* (2006.01)

(52) U.S. Cl. .................... 514/44; 424/143.1; 424/283.1; 536/24.5; 530/388.15; 530/388.22; 514/54; 514/73; 514/75; 514/99

(58) Field of Classification Search .................. None
See application file for complete search history.

(56) References Cited

U.S. PATENT DOCUMENTS 5,681,824 A    10/1997    Christ et al.

FOREIGN PATENT DOCUMENTS

WO    WO2005068442 A2    7/2005

OTHER PUBLICATIONS

Attal et al (Brain research, (Aug. 14, 1989) vol. 494, No. 2, pp. 276-284).*
Hutchinson et al (Eur. J. Neurosci. 28: 20-29, 2008).*
Apfel et al (Neuroscience 68(4): 1199-1206, 1995).*
Tanga et al (Proc. Nat. Acad. Sci. USA 102(16):5856-61, 1995).*
Huang et al., "Toll-like Receptors on Tumor Cells Facilitate Evasion of Immune Surveillance", Cancer Res. 2005 2005 65(12):5009-5014.
Mullarkey et al., "Inhibition of Endotoxin Response by E5564, a Novel Toll-Like Receptor 4-Directed Endotoxin Antagonist", J. Pharmacology and Experimental Therapeutics 2003 304(3):1093-1102.
Raghavendra et al., "Complete Freunds adjuvant-induced peripheral inflammation evokes glial activation and proinflammatory cytokine expressiobn in the CNS", European Journal of Neuroscience 2004 20:467-473.
Rudofsky et al., "Asp299Gly and Thr399Il3 Genotypes of the TLR4 Gene Are Associated With a Reduced Prevalence of Diabetic Neuropathy in Patients With Type 2 Diabetes", Diabetes Care 2004 27(1):179-183.
Tanga et al., "Quantitative real-time RT=PCT assessment of spinal microglial and astrocytic activation markers in a rat model of neuropathic pain", Neurochemistry International 2004 45:397-407.
Qi et al., "Toll-like Receptor 4 Signaling Regulates Cytosolic Phospholipase A2 Activation and Lipid Generation in Lipopolysaccharide-stimulated Macrophages", J. Biol. Chem. 2005 280(47):38969-38975.

* cited by examiner

*Primary Examiner* — Richard Schnizer
(74) *Attorney, Agent, or Firm* — Licata & Tyrrell P.C.

(57) ABSTRACT

The present invention is a method for preventing or treating neuropathic pain. Using an agent to decrease the expression or activity of Toll-like receptor 4 (TLR4), behavioral hypersensitivity is attenuated thereby preventing or treating neuropathic pain in a subject in need of such treatment.

1 Claim, 3 Drawing Sheets

```
                         SEQUENCE LISTING

<160> NUMBER OF SEQ ID NOS: 50

<210> SEQ ID NO 1
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 1
gatccgttcc attgcttggc gaatttcaag agaattcgcc aagcaatgga acttttttg      59

<210> SEQ ID NO 2
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 2
aattcaaaaa agttccattg cttggcgaat tctcttgaaa ttcgccaagc aatggaacg      59

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
gggaagctca ctggcatgg                                                  19

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 4
cttcttgatg tcatcatact tggcag                                          26

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
tcctaccccc aatgtgtccg tcgtg                                           25

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 6
gaccctgtcc gctcacgtat c                                    21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
tccacgcagt ccggtaaaat t                                    21

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
aacaacacac gcaggcgcac cc                                   22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
aaacttgcct tcaaaacctg gc                                   22

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
acctgaactc atcaatggtc acatc                                25

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
cacgtccatc ggttgatctt gggagaa                              27

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
ccagtcagct aaactcgctc aatc                                 24

<210> SEQ ID NO 13
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 13
tccagcctgt tgtaactgag atcc                                        24

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
aagggctgcc agccaagctc agc                                         23

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gagcgtgcag agatgatgga g                                           21

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
ttcagttcag ctgccagcg                                              19

<210> SEQ ID NO 17
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 17
atcgagaagg tccgcttcct ggaacag                                     27

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
gaaagacggc acacccacc                                              19

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 19
agacaaaccg cttttccatc ttc                                         23
```

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
tgcagctgga gagtgtggat cccaa                                        25

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
gttctcttca agggacaagg ctg                                          23

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
tcctggtatg agatagcaaa tcgg                                         24

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 23
tacgtgctcc tcacccacac cgtca                                        25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
gatgcattca tgagtattgc caagt                                        25

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
ttccggcaac agctggtg                                                18

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 26
caacccacag gtccagcgcc aag                                              23

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
cccccaatgt atccgttgtg                                                  20

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
tagcccagga tgccctttag t                                                21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
tgccgcctgg agaaacctgc c                                                21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
ctgcctcagg gatccgtaaa g                                                21

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 31
cctctgcctc aggaatgaca tc                                               22

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
cccgggacaa tgccgcgaa                                                   19

<210> SEQ ID NO 33
<211> LENGTH: 23
```

```
<212> TYPE: DNA
<213> ORGANISM: Artificial Sequence
<220> FEATURE:
<223> OTHER INFORMATION: Synthetic oligonucleotide

<400> SEQUENCE: 33
gattgctcag acatggcagt ttc                                              23

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
cactcgaggt aggtgtttct gctaa                                            25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
tccttgctga ggcagcaggt cgaat                                            25

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 36
gcaaacaggt cggcgtctt                                                   19

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
tgcgcagcgc taaaacttg                                                   19

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
tgatctcggc cctctgtccg ca                                               22

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tggccaccag taacatgcaa                                                  20
```

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
cagttggcgg cgatagtcat                                               20

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
cagacgttgc ttcccgcaac gc                                            22

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
gggactgatg ttgttgacag cc                                            22

<210> SEQ ID NO 43
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 43
catatgtaat taagcctccg acttgtg                                       27

<210> SEQ ID NO 44
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 44
tcacagagga taccacccac aacagaccag                                    30

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 45
ggaaggcagt gtcactcatt gtg                                           23

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

```
<400> SEQUENCE: 46
ggtcctcatc ctggaagctc c                                              21

<210> SEQ ID NO 47
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 47
aagctgtggc agctacctat gtcttgccc                                      29

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
ccccgactat gtgctcctca c                                              21

<210> SEQ ID NO 49
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 49
agggctcttg atggcgga                                                  18

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 50
cacaccgtca gccgatttgc cactt                                          25
```

METHOD FOR PREVENTING OR TREATING NEUROPATHIC PAIN

INTRODUCTION

This application claims benefit of U.S. Provisional Patent Application Ser. No. 60/786,643, filed Mar. 28, 2006, the content of which is incorporated herein by reference in its entirety.

This invention was made in the course of research sponsored by the National Institute of Drug Abuse (Grant No. DA11276). The U.S. government may have certain rights in this invention.

BACKGROUND OF THE INVENTION

Neuropathic pain remains a prevalent, persistent, and debilitating problem. Attempts to elucidate its mechanisms have focused principally on peripheral nerves, dorsal root ganglion, and central nervous system (CNS) neurons. Research efforts have expanded into the burgeoning field of glial/neuronal transmission and CNS immunologic responses to nerve injury. CNS glia display immune cell functions in both normal and pathologic conditions, and there is increasing evidence that neuropathic pain arising from nerve injury has a CNS neuroimmune component (DeLeo & Yezierski (2001) *Pain* 90:1-6; DeLeo, et al. (2004) *Neuroscientist* 10:40-52). Spinal glial activation triggers rapid, graded CNS expression of proinflammatory cytokines (including TNF-α, IL-1β, and IL-6) that contributes to the initiation and maintenance of behavioral hypersensitivity after L5 nerve transection (DeLeo & Yezierski (2001) supra; Vuong, et al. (2004) *Cell. Microbiol.* 6:269-275; Raghavendra, et al. (2004) *Neuropsychopharmacology* 29:327-334). The onset of proinflammatory cytokine expression correlates with microglial activation and the initiation of behavioral hypersensitivity (Sommer, et al. (1993) *J. Neuropathol. Exp. Neurol.* 52:223-233; Sommer & Myers (1995) *Acta Neuropathol.* 90:478-485; Popovich, et al. (1997) *J. Comp. Neurol.* 377:443-464; Popovich, et al. (1997) *J. Neuropathol. Exp. Neurol.* 56:1323-1338), and neuroimmune activation in painful neuropathy has been established (Vuong, et al. (2004) supra; Bennett (1999) *Proc. Natl. Acad. Sci. USA* 96:7737-7738; Bennett (2000) *Clin. J. Pain* 16:S139-S143). However, the mechanistic links between nerve injury, microglial activation, and the genesis of behavioral hypersensitivity is unclear.

Cells of the innate immune system, including monocytes/macrophages, natural killer cells, neutrophils, and microglia recognize invariant molecular structures of pathogens (termed pathogen-associated molecular patterns, PAMP) by means of stable, genetically conserved, pattern-recognition receptors on the cell surface. The genes producing these receptors are homologous to the Toll gene in *Drosophila* and are therefore termed Toll-like receptors (Akira & Sato (2003) *Scand J. Infect. Dis.* 35:555-562). Toll-like receptor 4 (TLR4) is a transmembrane receptor protein with extracellular leucine-rich repeat domains and a cytoplasmic signaling domain. TLR4 expression has been demonstrated in the rodent CNS (Laflamme & Rivest (2001) *FASEB J.* 15:155-163; Eklind, et al. (2001) *Eur. J. Neurosci.* 13:1101-1106), where in vivo and in vitro studies show that TLR4 is expressed by microglia (Lehnardt, et al. (2002) *J. Neurosci.* 22:2478-2486; Lehnardt, et al. (2003) *Proc. Natl. Acad. Sci. USA* 100:8514-8519). Lipopolysaccharide (LPS, a well known exogenous ligand for TLR4) and potential endogenous ligands for TLR4 (e.g., members of the heat shock protein family and proteoglycans) lead to NF-κB activation and subsequent induction of proinflammatory cytokines (Vabulas, et al. (2002) *J. Biol. Chem.* 277:15107-15112; Tsan & Gao (2004) *Am. J. Physiol.* 286:C739-C744). TLR4 gene expression is also significantly increased during all phases of inflammation and is suggested to be related to nerve injury-induced behavioral hypersensitivity (Raghavendra, et al. 2004. *Eur. J. Neurosci.* 20:467-473). Moreover, increased spinal microglial TLR4 activation correlates with the onset of behavioral hypersensitivity in rats after injury to the L5 spinal nerve, even in the absence of exogenous TLR4 ligands such as LPS (Tanga, et al. (2004) *Neurochem. Int.* 45:397-407).

Rudofsky, et al. ((2004) *Diabetes Care* 27:179-183) further teach that type II diabetics that are carriers of polymorphic forms of two TLR4 genes have a lower prevalence of diabetic neuropathy, wherein WO 2005/068442 discloses the use of certain compounds to treat pain in patients without TLR4 polymorphisms.

SUMMARY OF THE INVENTION

The present invention relates to a method of preventing or treating individuals suffering from neuropathic pain. The method involves administering to a subject in need of treatment an effective amount of an agent that decreases the expression or activity of TLR4 thereby preventing or treating neuropathic pain in the subject.

BRIEF DESCRIPTION OF THE DRAWINGS

FIG. 1 shows mechanical allodynia and thermal hyperalgesia in the L5 spinal nerve-transected mice. Shown are responses measured by foot-lift response frequency to stimulation with 0.008-g (FIG. 1A) and 0.015-g (FIG. 1B) von Frey filament. Paw-withdrawal latency (FIG. 1C) and tail-flick latency (FIG. 1D) are shown post-operatively. Mechanical allodynia and thermal hyperalgesia were significantly attenuated in KO mice (triangles; C57BL/10SCNJ; n=21) and TLR4 mutant mice (diamonds; C3H/HeJ; n=8) relative to their respective controls, i.e., TLR4 wild-type mice (square; C57BL10/ScSnJ; n=15) and C3H/HeN mice (circle; n=7).

DETAILED DESCRIPTION OF THE INVENTION

It has now been found that modulators of TLR4 can be used to attenuate behavioral hypersensitivity associated with neuropathic pain. Functional links between TLR4, microglial activation, and the initiation of behavioral hypersensitivity were assessed by analyzing glial activation and behavioral hypersensitivity after spinal L5 nerve transection in wild-type mice and in genetically manipulated mice lacking normal TLR4 expression. Two mouse strains with distinct genetic defects at the TLR4 loci were used, namely a TLR4 knockout (KO) mouse (C57BL/10ScNJ), which has a complete deletion of the TLR4 gene and thus cannot synthesize TLR4 mRNA or protein, and the TLR4 point-mutant mouse (C3H/HeJ), which expresses only a mutated (nonfunctional) TLR4 protein because of an amino acid substitution at position 712 in the third exon of the TLR4 gene (Poltorak, et al. (1998) *Science* 282:2085-2088; Poltorak, et al. (2000) *Proc. Natl. Acad. Sci. USA* 97:2163-2167). Glial activation and behavioral hypersensitivity after L5 nerve transection were also assessed in normal rats and in rats injected intrathecally with antisense oligodeoxynucleotide (ODN) to decrease CNS expression of TLR4. Both series of experiments established a role for TLR4 and CNS innate neuroimmune activation in the onset of behavioral hypersensitivity.

Figure 1A:
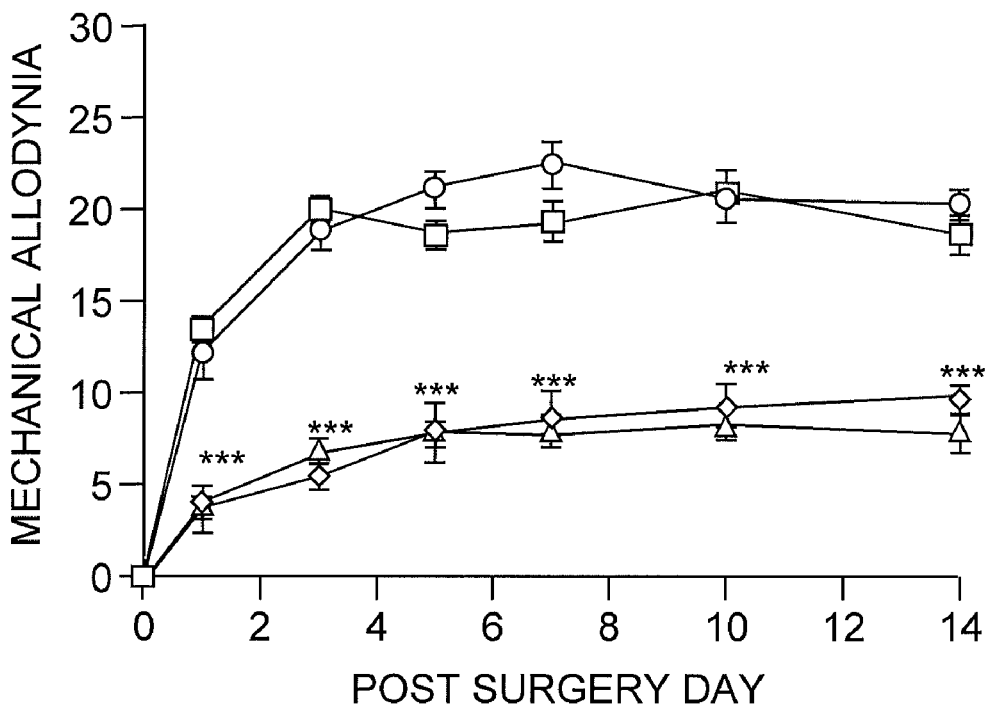
In FIGS. 1A and 1B, asterisks indicate significant attenuation in tactile allodynia compared with the wild-type controls (*, $P<0.001$; two-way ANOVA followed by Bonferroni post hoc test).
Figure 1B:
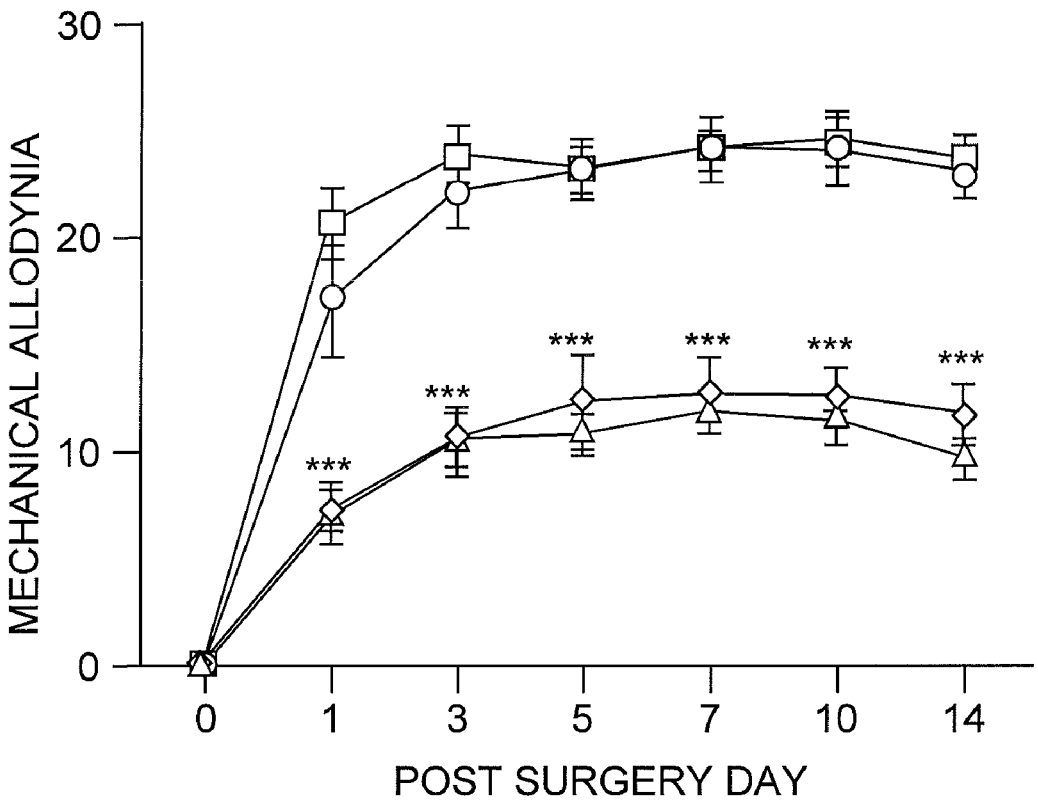
Figure 1C:
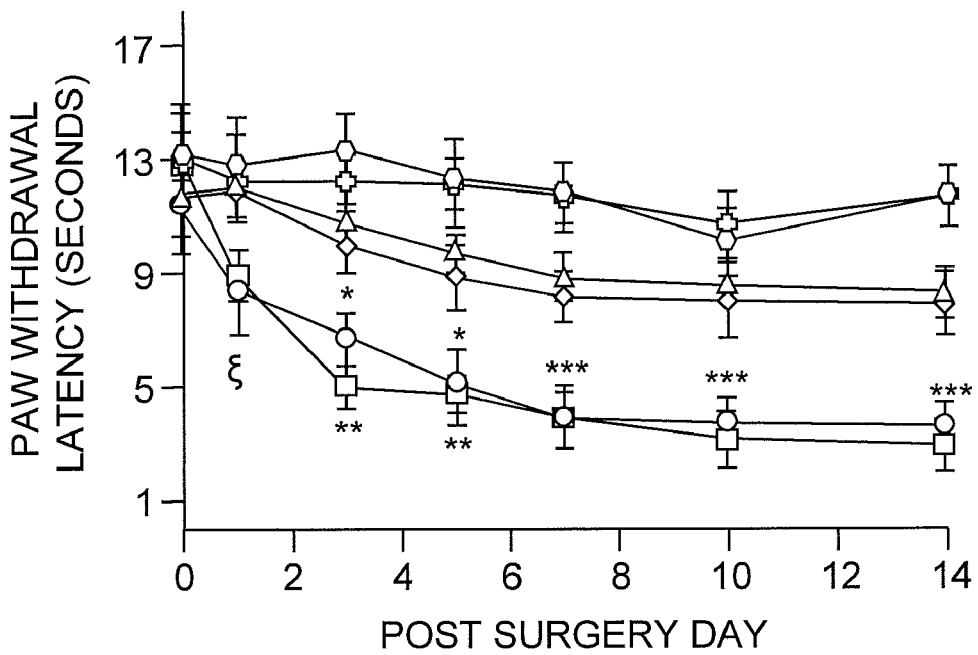
In FIGS. 1C and 1D, asterisks and ξ indicate significant decreases in paw-withdrawal and tail-flick latencies compared with wild type (*, $P<0.001$; **, $P<0.01$; *, $P<0.05$; ξ, $P<0.05$ vs. ScSnJ, two-way ANOVA followed by Bonferroni post hoc test). For FIGS. 1A and 1B, results are reported as the mean response frequency from three trials of 10 stimulations each ± SEM. For FIGS. 1C and 1D, the results are reported as the mean latency response time of three stimulations ± SEM, and hexagon represents uninjured SCNJ (n=6) and "+" symbol represents uninjured ScSnJ (n=6).
Figure 1D:
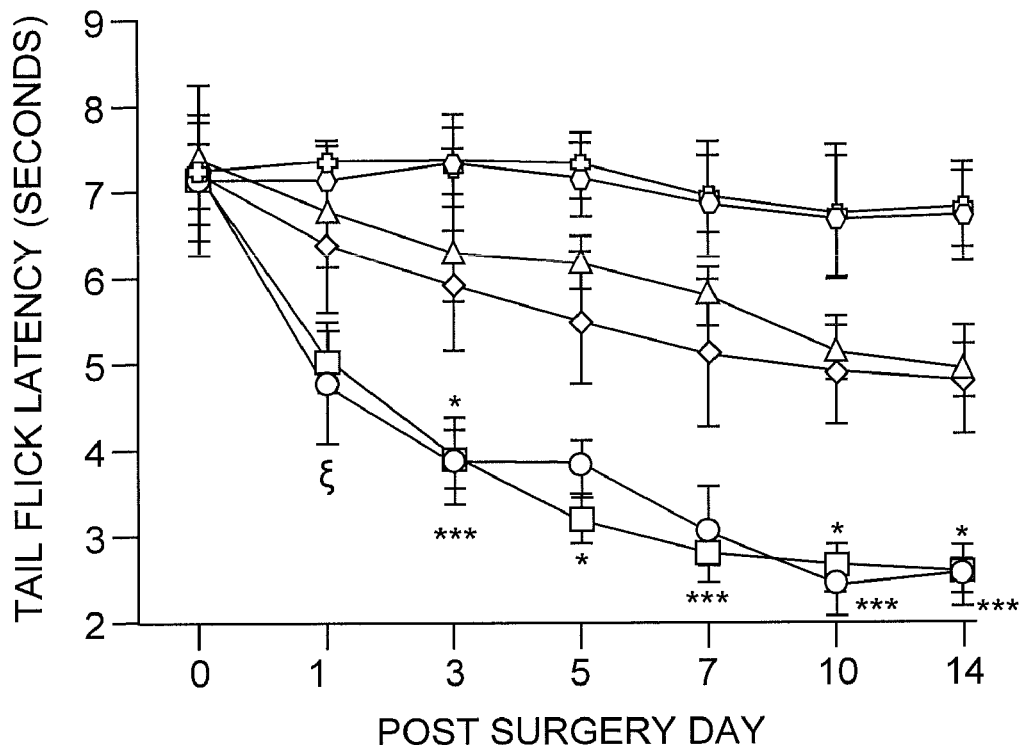

To demonstrate that TLR4 was critical for pain induction, TLR4 KO mice (C57BL/10SCNJ; n=21) and point-mutant mice were analyzed. TLR4 KO mice (C57BL/10SCNJ; n=21) and point-mutant mice (C3H/HeJ; n=8) displayed significantly attenuated mechanical allodynia compared with their respective wild-type controls (C57BL10/ScSnJ; n=15 and C3H/HeN; n=7) for 0.008-g ($P<0.001$) and 0.015-g ($P<0.001$) von Frey filament stimulations beginning at day 1 after surgery (FIGS. 1A and 1B). FIG. 1C shows that TLR4 KO and point-mutant mice also displayed a significantly attenuated response to heat for days 1-7 ($P<0.05$) and 10-14 after surgery ($P<0.001$). FIG. 1D shows that the tail-flick response to immersion in 49° C. water was also significantly attenuated for these mice for days 1-7 ($P<0.05$) and 10-14 after surgery ($P<0.001$).

To determine whether knockout of TLR4 could attenuate spinal glial activation, expression of CD11b and CD14 was analyzed. A 3- to 5-fold decrease in expression of mRNA for CD11b and CD14 was observed in TLR4 KO mice compared with the wild-type control group beginning at day 3 after surgery ($P<0.001$). A graded, significant up-regulation of TLR4 mRNA was observed in the wild-type control group ($P<0.001$). No TLR4 mRNA was detected in the TLR4 KO mice. Messenger RNA for the astrocytic activation marker glial fibrillary acid protein (GFAP) also decreased in TLR4 KO mice relative to the wild-type control group, starting at day 7 after surgery ($P<0.001$).

A link between innate immunity and spinal proinflammatory cytokine expression was also established. Significantly (3- to 5-fold) lower spinal expression of mRNA for IFN-γ, IL-1β, and TNF-α was observed after injury in the TLR4 KO mice as compared with the wild-type control group ($P<0.001$).

In injured wild-type mice, a robust immunoreactive staining of CD11b/CR3 throughout the dorsal horn ipsilateral to the L5 nerve transection (laminae I-IV) was observed on days 3, 7, and 14 after surgery. By contrast, CD11b/CR3 immunoreactivity was reduced almost to baseline levels in the ipsilateral dorsal horn of injured TLR4 KO mice. These immunohistochemical protein data support the mRNA findings for CD11b and establish a link between microglial activation and TLR4.

Figure 2A:
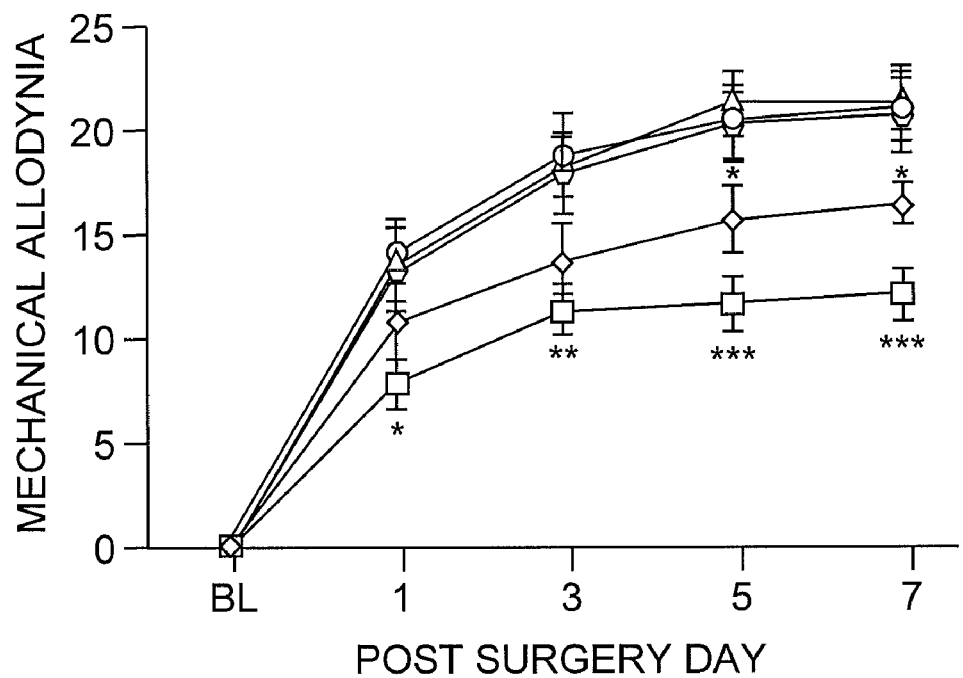
FIG. 2 shows a dose-response relationship after daily intrathecal administration of TLR4 antisense ODN in L5 spinal nerve-transected rats. The effect of a daily intrathecal injection of two doses of TLR4 antisense ODN (10 μg per day, diamond; 20 μg per day, square), mismatch ODN (10 μg per day, circle; 20 μg per day, hexagon), or saline solution (triangle) on mechanical allodynia (FIG. 2A) and paw-withdrawal latencies (FIG. 2B) is shown. Thermal and tactile hypersensitivity were significantly attenuated in a dose-dependent manner compared with saline and mismatch ODN-treated rats with marked attenuation observed with 10-μg daily injections of TLR4 antisense ODN starting at days 3-7 ($P<0.05$ and $P<0.01$) and day 1 (*, $P<0.05$), day 3 (, $P<0.01$), and through day 7 (*, $P<0.001$) for 20-μg daily injection of TLR4 antisense ODN (two-way ANOVA followed by Bonferroni post hoc test).
Figure 2B:
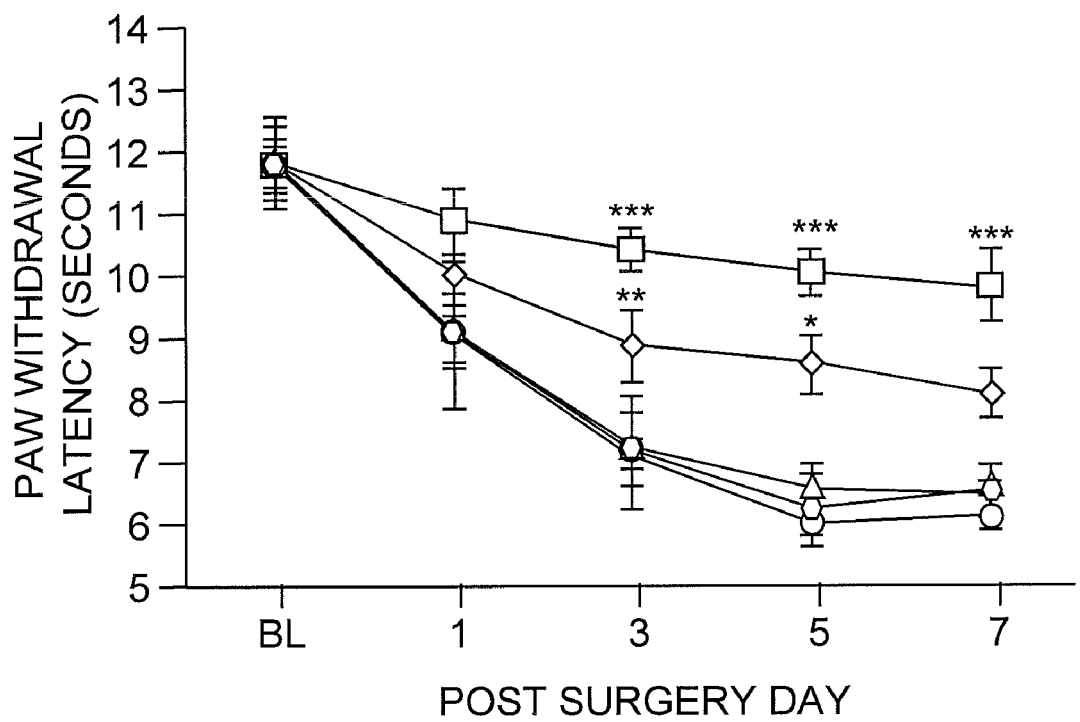

To demonstrate that behavioral hypersensitivity could be attenuated using a small molecule inhibitor, a TLR4 antisense oligodeoxynucleotide (ODN) was injected into the CNS of rats. It was initially confirmed that FITC-labeled random control ODN was incorporated into the spinal cord. Co-labeling with DAPI demonstrated the proximity of the FITC-labeled ODN to the nucleus, showing that the modified ODN was incorporated into the CNS parenchyma. Daily intrathecal injection of 10 μg of TLR4 antisense ODN resulted in moderate but significant attenuation of both mechanical allodynia (FIG. 2A) and thermal hyperalgesia (FIG. 2B); more significant attenuation was observed with 20-μg daily injections ($P<0.001$). Daily injections of saline or of 10 or 20 μg of mismatch ODN did not alter mechanical or thermal hypersensitivity.

Because of the potential for TLR4 antisense ODN backbone toxicity, the maximum daily intrathecal administration of TLR4 antisense ODN was 20 μg. This dosage provided a 56% decrease in spinal TLR4 mRNA expression ($P<0.001$). Decreased expression of TLR4 paralleled the decreased expression of the microglial activation markers CD11b (51%) and CD14 (44%) ($P<0.001$). The decrease in TLR4 also led to a significant decrease in proinflammatory cytokines, i.e., TNF-α (17%), IL-6 (52%), and IL-1β (53%); $P<0.001$ in all cases in TLR4 antisense ODN-treated rats as compared with rats treated with saline or mismatch ODN.

The data presented herein demonstrate a key role for microglial TLR4 in the induction of behavioral hypersensitivity in rodent models of neuropathy. These data also show that the mRNA expression of the microglial activation markers, TLR4, CD11b/CR3, and CD14, were only elevated at the initiation phase of behavioral hypersensitivity (days 3 and 7). Conversely, the astrocytic activation marker GFAP showed an opposite pattern with a graded increase in the mRNA expression level at later time points (days 7 and 14). These results are consistent with findings suggesting that microglia are involved in the initiating phase of behavioral hypersensitivity, whereas astrocytes are involved in the maintenance phase (Tanga, et al. (2004) *Neurochem. Int.* 45:397-407; Raghavendra, et al. (2003) *J. Pharmacol. Exp. Ther.* 306:624-630). Many factors have been postulated to activate microglia after injury, but the finding that microglial TLR4 plays a crucial part as a receptor in the induction phase of behavioral hypersensitivity in rodent models of neuropathy has not been suggested in the art.

After L5 nerve transection injury, mediators are released or activated, causing secondary swelling and damage to neurons. Such mediators include ATP, glutamate, acidosis, free saturated or unsaturated fatty acids, high-extracellular potassium, serotonin, bradykinin, substance P, histamine, and products from the cyclooygenase and lipoxygenase pathway of the arachidonic acid metabolism (Kempski & Volk (1994) *Acta Neurochir.* Suppl. 60:7-11). At the spinal cord level, these alterations lead to a hyperexcitable state with intense nociceptive input to the dorsal horn and the chemical sensitization of high-threshold nociceptors to transmit low-intensity nonnoxious stimuli.

The findings presented herein indicate that TLR4 is a microglial sensor that triggers glial activation and the dynamic CNS immune response that ensues in response to nerve damage. Inhibition of TLR4 expression was found to produce a significant and dose-related attenuation of L5 nerve transection-induced tactile and thermal hypersensitivity, reduce expression of mRNA for microglial markers, and reduce expression of mRNA for spinal proinflammatory cytokine. These findings indicate a CNS role for TLR4 and innate immunity in the etiology of neuropathic pain. The ability of TLR4 to activate a pathway leading to central sensitization and nerve injury-induced behavioral hypersensitivity provides a means for regulating glial activation, and thus, alleviating chronic pain due to nerve damage. Accordingly, the present invention relates to methods for attenuating behavioral hypersensitivity associated with neuropathic pain and for preventing or treating neuropathic pain using an effective amount of an agent that decreases the expression or activity of TLR4. As used in the context of the present invention, neuropathic pain is pain that originates from a damaged nerve or nervous system.

Generally, an agent of the present invention is administered to an individual or patient identified as being in need of such prevention or treatment using routes (e.g., injection, infusion, or inhalation) and dosages that are determined to be appropriate by those of skill in this art. As used in the context of the present invention, an individual in need of treatment can include a human, zoo animal, companion animal, laboratory animal or livestock.

An effective amount of agent administered is defined as an amount which prevents, attenuates, or reduces behavioral hypersensitivity associated with neuropathic pain. Behavioral hypersensitivity of pain may include sensations that are sharp, aching, throbbing, gnawing, deep, squeezing, or colicky in nature and can be measured by, for example, exposure to thermal hyperalgesia or mechanical hyperalgesia.

As will be understood by those of skill in this art, the specific dose level for any particular patient will depend on a variety of factors, including the activity of the specific compound employed; the age, body weight, general health, and sex of the individual being treated; the time and route of administration; the rate of excretion; other drugs that have previously been administered; and the severity of the particular disease undergoing therapy.

The method of the present invention is particularly useful for preventing and/or treating pain associated with neuropathies, polyneuropathies (e.g., as in diabetes and trauma), neuralgias (e.g., post-zosterian neuralgia, postherpetic neuralgia, trigeminal neuralgia, algodystrophy, and HIV-related pain); musculo-skeletal pain such as osteo-traumatic pain, arthritis, osteoarthritis, spondylarthritis as well as phantom limb pain, back pain, vertebral pain, post-surgery pain; cancer-related pain; vascular pain such as pain resulting from Raynaud's syndrome, Horton's disease, arteritis, and varicose ulcers; as well as pain associated with multiple sclerosis, Crohn's Disease, and endometriosis.

Agents for decreasing the expression or activity of TLR4 can be selected from a variety of compound classes including small organic molecules, antisense oligonucleotides (including siRNA and the like), ribozymes, anti-TLR4 antibodies or fragments thereof. In particular embodiments, the instant agent decreases the expression or activity of TLR4 receptor by 10% to 100% (e.g., 10%, 20%, 30%, 40%, 50%, 60%, 70%, 80%, 90%, 95%, or 100%) relative to a control level of TLR4 expression or activity such as that found in a subject with neuropathic pain and has not received treatment.

Agents known in the art to antagonize the activity of TLR4 include, but are not limited to, E5564 (also known as compound 1287 or SGEA) (Mullarkey et al. (2003) *J. Pharmacol. Exp. Ther.* 304(3):1093-1102, 2003). This agent is also described in U.S. Pat. No. 5,681,824. A cell-permeable TLR4 inhibitory peptide is also known in the art for blocking TLR4 activity (see Huang, et al. (2005) *Cancer Research* 65:5009-5014). Antagonistic antibodies such as monoclonal antibody MTS510 to mouse TLR4 (commercially available from eBioscience, San Diego, Calif.) can also be used. See, e.g., Qi & Shelhamer (2005) *J. Biol. Chem.* 280:38969-38975. For therapeutic use in species such as humans, such an antibody can be humanized or fragmented to improve efficacy.

Agents which inhibit the expression of TLR4 include, e.g., TLR4 antisense ODN as well as TLR4 short interfering RNAs (siRNAs). Antisense ODN molecules are commercially available to the skilled artisan from sources such as Biognostik (Göttingen, Germany), whereas suitable siRNA molecules are disclosed by Huang, et al. (2005) supra or Qi & Shelhamer (2005) supra (e.g., sense, gat ccG TTC CAT TGC TTG GCG AAT TTC AAG AGA ATT CGC CAA GCA ATG GAA CTT TTT Tg (SEQ ID NO:1) and antisense, aat tcA AAA AAG TTC CAT TGC TTG GCG AAT TCT CTT GAA ATT CGC CAA GCA ATG GAA Cg (SEQ ID NO:2)). As will be appreciated by the skilled artisan, antisense ODN, siRNA, or ribozymes can be readily generated based on the known nucleic acid sequence encoding TLR4. Examples of known TLR4 sequences are found in GENBANK, including those having the following Accession Nos. (listed by species): cow (*Bos taurus*; NM_174198, AB056444, and AF310952); pig (*Sus scrofa*; AY289532); chicken (*Gallus gallus*; AY064697); horse (*Equus caballus*; AY005808); dog (*Canis farniliaris*; AB080363); cat (*Felis catus*; BAB43947); human (*Homo sapiens*; NM_138557, NM_138556, NM_138554, NM_003266, AF177765, AF172171, AF172170, AF172169, AH009665, AF177766, and U88880); mouse (*Mus musculus*; NM021297, AL805946, AF177767, AF222309, AF185285, AF110133, and AF095353); rat (*Rattus norvegicus*; NM_019178); Chinese hamster (*Cricetulus griseus*; AF153676); gorilla (*Gorilla gorilla*; AF497565, AF497564, AF497563, and AH011592); orangutan (*Pongo pygmaeus*; AF497562, AF497561, AF497560, and AH011591); olive baboon (*Papio hamadryas anubis*; AH008378, AF180964, AF180963, and AF180962); pygmy chimpanzee (*Pan paniscus*; AH008351, AF179220, AF179219, and AF179218); and rhesus monkey (*Macaca rnulatta*; AF162474).

It is contemplated that the agents of the present invention can be used alone or in combination with other treatments known to alleviate pain.

The invention is described in greater detail by the following non-limiting examples.

EXAMPLE 1

Animals

Mice. C57BL/10ScNJ mice (TLR4-deleted; n=21) have a homozygous deletion of 74 kb at the tlr4 locus that removes all three TLR4 exons (Poltorak, et al. (1998) supra). C3H/HeJ mice (TLR4-deficient; n=8) possess a dominant-negative point mutation Pro->His at position 712 in the third exon of the TLR4 gene (Poltorak, et al. (1998) supra). C57BL/10Sc-SnJ (n=15) and C3H/HeN (n=7) mice are the respective wild-type controls. The C57BL/10ScNJ, C57BL/10ScSnJ, and C3H/HeJ strains were purchased from The Jackson Laboratory, and the C3H/HeN strain was purchased from Charles River Laboratories. All mice weighed 25-30 grams at the time of surgery.

Rats. Male Sprague-Dawley rats (n=48) purchased from Harlan (Indianapolis, Ind.) were used. All weighed 200-250 grams at the time of surgery.

In accordance with the guidelines set forth by the International Association for the Study of Pain, efforts were made throughout to minimize animal discomfort and to use the fewest animals needed for statistical significance. Animals were housed on a 12-hour light, 12-hour dark cycle with food and water available ad *libitum*.

EXAMPLE 2

Surgery

Animals were anesthetized with halothane in an $O_2$ carrier (induction, 4% and maintenance, 2%). A small incision to the skin overlaying L5-S1 was made, followed by retraction of the paravertebral musculature from the vertebral transverse processes. The L6 transverse process was partially removed, exposing the L4 and L5 spinal nerves. The L5 spinal nerve was identified, lifted slightly, and transected. The wound was irrigated with saline and closed in two layers with 3-0 polyester suture (fascial plane) and surgical skin staples.

EXAMPLE 3

Behavioral Testing

For mice, mechanical sensitivity was assessed by applying 0.008- and 0.015-g von Frey filaments (Stoelting, Wood Dale, Ill.) on the plantar surface of the ipsilateral hind paw. For rats, 2- and 12-g von Frey filaments were used. These stimuli are normally nonnoxious. Allodynia was characterized as the number of paw withdrawals in three sets of 10 stimulations each, and was tested on days 1, 3, 5, 7, 10, and 14 after surgery for mice and on days 1, 3, 5, and 7 for rats. Thermal sensitivity was determined by using paw-withdrawal latencies to radiant heat and tail-flick latencies to tail immersion in hot water (49° C.). Three tail-flick and paw-withdrawal latencies were obtained per animal for each testing session. Animals were tested for baseline responses three times before undergoing the L5 spinal nerve transection surgery.

EXAMPLE 4

Intratecal Oligodeoxynucleotide Administration

TLR4 antisense ODN, mismatch ODN, and a random control oligonucleotide labeled with FITC were obtained by Biognostik (Göttingen, Germany). The oligonucleotide was resuspended in sterile phosphate-buffered saline (PBS) at a final concentration of 1 µg/µl for mismatch ODN and 2 µg/µl for antisense ODN. The L5 spinal nerve transection model in rats was employed. The rats were divided into three groups based on the final amount of ODN intrathecally administered. In the first group, rats were administered antisense ODN (10 µg/day; n=8), mismatch ODN (10 µg/day; n=8), or saline (n=8), and tested separately. In the second group, rats were administered antisense ODN (20 µg/day; n=8), mismatch ODN (20 µg/day; n=8), or saline (n=8). All rats in both groups underwent L5 nerve transection surgery, and, after daily behavioral testing that took place between 8:00 and 10:00 a.m., were administered ODN intrathecally by means of lumbar puncture under brief inhalational anesthesia for 7 days starting 1 day before surgery. In the third group, 20 µg of FITC-labeled random oligonucleotide was injected intrathecally by means of lumbar puncture in three rats. These rats were killed at 4, 8, or 12 hours after injection to determine the optimal cellular uptake time of FITC-labeled oligonucleotide. The injection volume was 10 µl followed by a 15-µl sterile PBS wash.

The ODN solutions were aliquoted in sterile 1.5-ml EPPENDORF tubes. The aliquots were stored at −20° C., and three aliquots were taken out daily during the 7 days of intrathecal administration. The experimenter was blind to their content throughout the study. Behavioral testing was carried out 1 hour before the administration of TLR4 antisense ODN, mismatch ODN, or saline. All rats in groups 1 and 2 were killed on day 7 after surgery, 1 day after the final intrathecal administration of TLR4 antisense ODN, mismatch ODN, or saline.

EXAMPLE 5

Real-Time RT-PCR

To test for a direct link between TLR4 expression, microglial activation, and proinflammatory cytokine expression, established quantitative RT-PCR methods (Tanga, et al. (2004) supra) were used to measure levels of mRNA for TLR4, CD11b, CD14, IL-1β, IL-6, and TNF-α in homogenates from lumbar spinal cord tissue. Briefly, the animals were killed by carbon dioxide asphyxiation followed by decapitation on days 3, 7, and 14 after surgery for mice and on day 7 for rats. The spinal cord tissue was flushed out with PBS by using a 15-ml syringe and 18-gauge needle. The harvested cords were immediately snap-frozen to −51° C. and stored at −80° C. before RNA isolation. Total RNA was isolated from the L5 lumbar spinal cord tissue and processed for RT-PCR. Primer and TAQMAN probe sequences for the mouse genes are listed in Table 1, whereas rat genes are listed Table 2. The primers and probes selected for this experiment met the G+C content requirement and had melting temperatures of 60° C. and 70° C., respectively.

TABLE 1

| Gene | Primer/Probe | Sequence | SEQ ID NO: | GENBANK Acc. No. |
|---|---|---|---|---|
| GADPH | F Primer | GGGAAGCTCACTGGCATGG | 3 | XM_111622 |
|  | R Primer | CTTCTTGATGTCATCATACTTGGCAG | 4 |  |
|  | Probe* | TCCTACCCCAATGTGTCCGTCGTG | 5 |  |
| CD11b (ITGAM) | F Primer | GACCCTGTCCGCTCACGTATC | 6 | NM_008401 |
|  | R Primer | TCCACGCAGTCCGGTAAAATT | 7 |  |
|  | Probe | AACAACACACGCAGGCGCACCC | 8 |  |
| TLR4 | F Primer | AAACTTGCCTTCAAAACCTGGC | 9 | AF185285 |
|  | R Primer | ACCTGAACTCATCAATGGTCACATC | 10 |  |
|  | Probe | CACGTCCATCGGTTGATCTTGGGAGAA | 11 |  |

TABLE 1-continued

| Gene | Primer/Probe | Sequence | SEQ ID NO: | GENBANK Acc. No. |
|---|---|---|---|---|
| CD14 | F Primer | CCAGTCAGCTAAACTCGCTCAATC | 12 | BC057889 |
| | R Primer | TCCAGCCTGTTGTAACTGAGATCC | 13 | |
| | Probe | AAGGGCTGCCAGCCAAGCTCAGC | 14 | |
| GFAP | F Primer | GAGCGTGCAGAGATGATGGAG | 15 | AF332062 |
| | R Primer | TTCAGTTCAGCTGCCAGCG | 16 | |
| | Probe | ATCGAGAAGGTCCGCTTCCTGGAACAG | 17 | |
| IL-1β | F Primer | GAAAGACGGCACACCCACC | 18 | M15131 |
| | R Primer | AGACAAACCGCTTTTCCATCTTC | 19 | |
| | Probe | TGCAGCTGGAGAGTGTGGATCCCAA | 20 | |
| TNF-α | F Primer | GTTCTCTTCAAGGGACAAGGCTG | 21 | NM_013693 |
| | R Primer | TCCTGGTATGAGATAGCAAATCGG | 22 | |
| | Probe | TACGTGCTCCTCACCCACACCGTCA | 23 | |
| INF-γ | F Primer | GATGCATTCATGAGTATTGCCAAGT | 24 | NM_008337 |
| | R Primer | TTCCGGCAACAGCTGGTG | 25 | |
| | Probe | CAACCCACAGGTCCAGCGCCAAG | 26 | |

*The TAQMAN probe has a reporter fluorescent dye, 6-carboxyfluorescein (FAM), at the 5' end, and a fluorescence dye quencher, 6-carboxytetramethylrhodamine (TAMRA), at the 3' end.

TABLE 2

| Gene | Primer/Probe | Sequence | SEQ ID NO: | GENBANK Acc. No. |
|---|---|---|---|---|
| GADPH | F Primer | CCCCCAATGTATCCGTTGTG | 27 | NM_01008 |
| | R Primer | TAGCCCAGGATGCCCTTTAGT | 28 | |
| | Probe* | TGCCGCCTGGAGAAACCTGCC | 29 | |
| CD11b (ITGAM) | F Primer | CTGCCTCAGGGATCCGTAAAG | 30 | U59801 |
| | R Primer | CCTCTGCCTCAGGAATGACATC | 31 | |
| | Probe | CCCGGGACAATGCCGCGAA | 32 | |
| TLR4 | F Primer | GATTGCTCAGACATGGCAGTTTC | 33 | NM_0191178 |
| | R Primer | CACTCGAGGTAGGTGTTTCTGCTAA | 34 | |
| | Probe | TCCTTGCTGAGGCAGCAGGTCGAAT | 35 | |
| CD14 | F Primer | GCAAACAGGTCGGCGTCTT | 36 | AF087943 |
| | R Primer | TGCGCAGCGCTAAAACTTG | 37 | |
| | Probe | TGATCTCGGCCCTCTGTCCGCA | 38 | |
| GFAP | F Primer | TGGCCACCAGTAACATGCAA | 39 | NM_017009 |
| | R Primer | CAGTTGGCGGCGATAGTCAT | 40 | |
| | Probe | CAGACGTTGCTTCCCGCAACGC | 41 | |
| IL-6 | F Primer | GGGACTGATGTTGTTGACAGCC | 42 | NM_012589 |
| | R Primer | CATATGTAATTAAGCCTCCGACTTGTG | 43 | |
| | Probe | TCACAGAGGATACCACCCACAACAGACCAG | 44 | |
| IL-1b | F Primer | GGAAGGCAGTGTCACTCATTGTG | 45 | NM_031512 |
| | R Primer | GGTCCTCATCCTGGAAGCTCC | 46 | |
| | Probe | AAGCTGTGGCAGCTACCTATGTCTTGCCC | 47 | |
| TNF-α | F Primer | CCCCGACTATGTGCTCCTCAC | 48 | AF329987 |
| | R Primer | AGGGCTCTTGATGGCGGA | 49 | |
| | Probe | CACACCGTCAGCCGATTTGCCACTT | 50 | |

*The TAQMAN probe has the reporter fluorescent dye FAM at the 5' end, and the fluorescence dye quencher TAMRA at the 3' end.

EXAMPLE 6

Immunohistochemistry

To assess the time course of CD11b/CR3 immunoreactivity, a separate group of mice containing C57BL/10ScNJ (KO) mice and C57BL/10ScSnJ (wild-type) mice, four injured and two uninjured per strain, was perfused transcardially with 0.1 M PBS followed by 4% paraformaldehyde in PBS on days 3, 7, and 14 after surgery. The L5 segment of the spinal cord was harvested by means of a laminectomy. Immunohistochemistry was performed on transverse 20-μm L5 spinal cord sections by using an avidin-biotin complex technique known in the art (Colburn, et al. (1999) *Exp. Neurol.* 157:289-304). A monoclonal antibody for CD11b was used to label the time-course expression of CD11b/CR3 on activated microglia (1:500 working dilution, Serotec, Raleigh, N.C.).

EXAMPLE 7

Statistical Analysis

The statistical significance of differences between TLR4 KO, point-mutant, TLR4 antisense ODN-treated, and control animals was determined by using multivariate two-way ANOVA followed by post hoc Bonferroni analysis. All statistical analyses were performed by using PRISM 4.01 (GRAPHPAD, San Diego, Calif.). A P value of <0.05 was considered significant.

---

What is claimed is:

1. A method of preventing or treating neuropathic pain comprising administering intrathecally to a subject in need of treatment an effective amount of an agent that decreases the expression or activity of TLR4, wherein said agent comprises a TLR4 antisense oligonucleotide, MTS510, or E5564, thereby preventing or treating neuropathic pain in the subject.

* * * * *